United States Patent [19]

Scully

[11] 4,191,468
[45] Mar. 4, 1980

[54] RANGE FINDING FIBERSCOPE

[75] Inventor: John F. Scully, Spencer, Mass.

[73] Assignee: American Optical Corporation, Southbridge, Mass.

[21] Appl. No.: 917,612

[22] Filed: Jun. 21, 1978

[51] Int. Cl.² .............................................. G01C 3/12
[52] U.S. Cl. .......................................... 356/17; 356/18
[58] Field of Search ........................ 356/1, 3, 9, 17, 18

[56] References Cited

U.S. PATENT DOCUMENTS

| 3,091,235 | 5/1963 | Richards | 128/6 |
|---|---|---|---|
| 3,162,214 | 12/1964 | Bazinet | 138/120 |
| 3,614,228 | 10/1971 | Lyon | 356/17 |
| 3,744,906 | 7/1973 | Sato et al. | 356/3 |
| 3,819,267 | 6/1974 | Kawahara | 356/3 |
| 3,913,568 | 10/1975 | Carpenter | 128/11 |

Primary Examiner—John K. Corbin
Assistant Examiner—R. A. Rosenberger
Attorney, Agent, or Firm—Jeremiah J. Duggan; Alan H. Spencer; Stephen A. Schneeberger

[57] ABSTRACT

A range finding fiberscope for measuring the distance of a point in space from a reference plane. The device is adaptable to use in confined spaces and has a variety of applications including industrial, medical and photographic.

10 Claims, 3 Drawing Figures

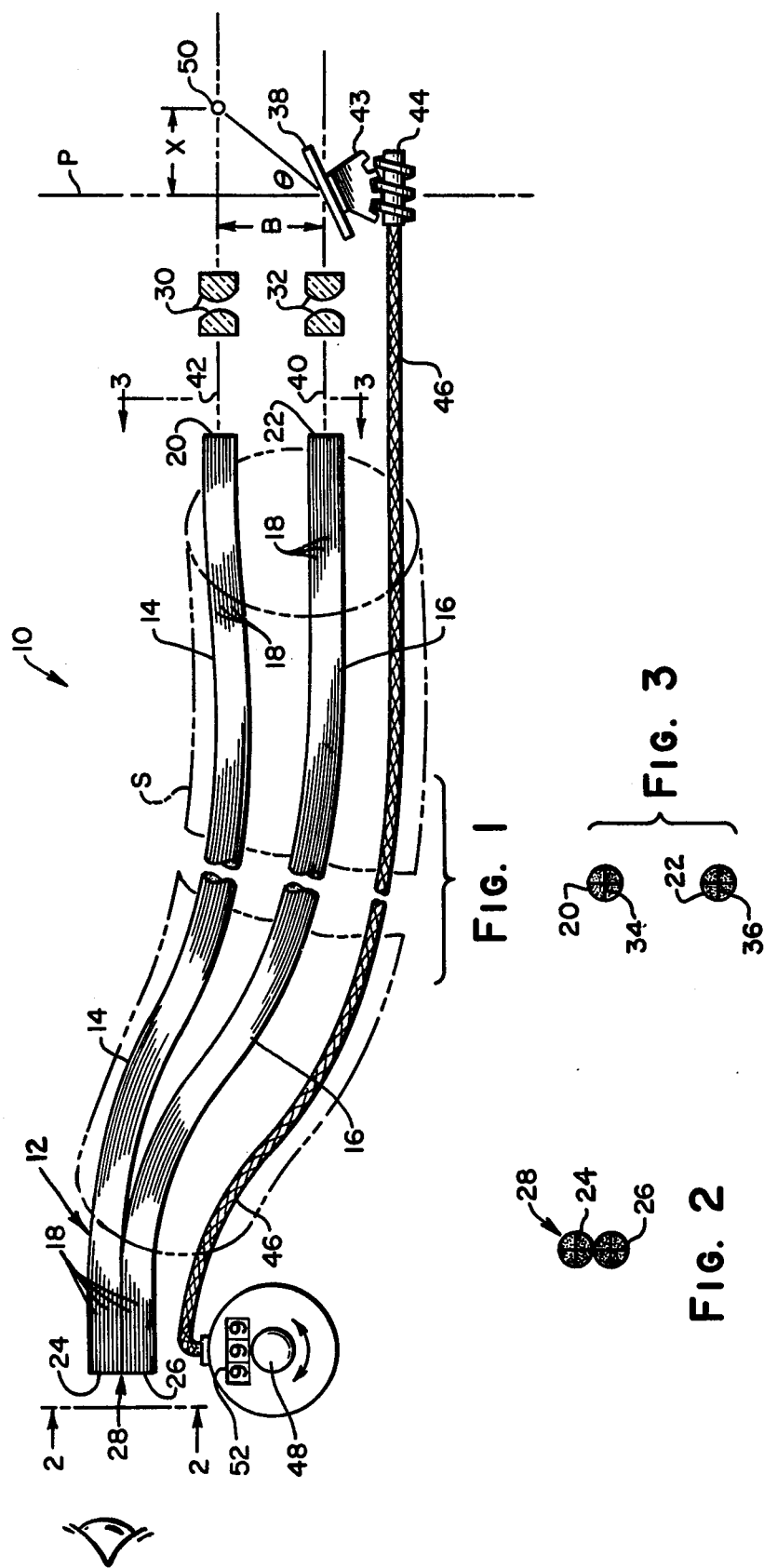

RANGE FINDING FIBERSCOPE

BACKGROUND OF THE INVENTION

1. Field of the Invention

Fiber optical instruments with particular reference to a fiber optic range finding fiberscope.

2. Discussion of the Prior Art

Endoscopes have long been used in various professions and industries to examine confined spaces and in recent years have been afforded the advantage of flexibility by incorporation of image-conducting optical fiber bundles.

In the examination of confined areas it is often necessary to make measurements of distances from a reference plane to points under examination. This, however, has been problematic in that heretofore the point to be measured had to be reached with the end of a measuring probe, the distal end of the endoscope or other such measuring means. These prior art procedures are hindered by general ungainliness of apparatus, lack of optimum measuring precision and difficulty, if not inability, to accurately measure distances to points which can be viewed but not reached.

Accordingly, it is an object of the present invention to provide novel means for simply and accurately measuring the distance from a point in space to a reference plane, more particularly in confined areas.

Another object is to accomplish the foregoing with flexible endoscopic means and without need for reaching the point to be measured.

Still another object is to provide novel range finding means for obtaining precision distance measurements without need for special operator training or skills.

Other objects and advantages of the invention will become more readily apparent from the following description.

SUMMARY OF THE INVENTION

The foregoing objects and their corollaries are accomplished by the provision of a range finding fiberscope comprising a bifurcated flexible bundle of optical fibers each branch of which is adapted to conduct optical images independently of the other. The branches are proximally juxtapositioned and distally spaced a fixed pre-established distance apart on centers, the centers being established by cross hairs preferably applied directly to each mosaic of distal ends of respective branch bundle fibers.

Objective lens means disposed forwardly of each distal fiber mosaic serves to form images of spaced objects thereupon.

Forwardly of one objective is an angularly adjustable light-deflector (e.g. mirror) which establishes the location of a reference plane from which range finding measurements may be taken with the fiberscope.

With an image of a point to be measured formed by the other objective and centered upon cross hairs of its adjacent mosaic of distal fibers, e.g. by movement of the whole fiberscope, and a second image of the same point brought to a centered relationship with cross hairs on the other mosaic of fibers by angular adjustment of the light-deflector the extent of the light-deflector adjustment corresponds to distance from the point to be measured to the reference plane. Direct dial reading of distance measured is contemplated.

Details of the invention will become more readily apparent from the following description when taken in conjunction with the accompanying drawings.

IN THE DRAWINGS

FIG. 1 is a diagrammatic illustration of a preferred embodiment of the invention;

FIG. 2 is a view of the range finding fiberscope of FIG. 1 taken from the position of line 2—2 and looking in the direction of the arrows; and FIG. 3 is a view similar to FIG. 2 taken from line 3—3 of FIG. 1, looking in the direction of the arrows.

DESCRIPTION OF THE PREFERRED EMBODIMENTS

Referring more particularly to FIG. 1 of the drawings, range finding fiberscope 10 comprises a bifurcated or dual image-conducting fiber optic component 12. Legs 14 and 16 of component 12 are each formed of a multiplicity of juxtapositioned optical light-conducting fibers 18. Opposite ends of fibers 18 of each leg 14 and 16 are identically geometrically patterned, the mosaics of which function as image receiving and emitting faces 20, 22 and 24, 26 respectively.

Component 12 is flexible throughout the intermediate portions of legs 14 and 16 and image-emitting faces 24 and 26 are preferably closely juxtapositioned to jointly provide a dual-image viewing screen 28 (FIG. 2) at the proximal end of component 12. If desired, an eyepiece (not shown) may be provided to facilitate the viewing of images upon screen 28.

Opposite distal faces 20 and 22 of component 12 are fixedly spaced a predetermined distance apart. Located forwardly of each face 20 and 22 are objective lens means 30 and 32 respectively. Images of points spaced forwardly of objectives 30 and 32 are focused thereby upon respective faces 20 and 22.

To facilitate the centering of images of points in space which are focused upon faces 20 and 22, crosshairs 34 and 36 (FIG. 3) are provided. As illustrated in FIG. 2, images of the crosshairs are transmitted by total internal reflection through fibers 18 to emitting faces 24 and 26 of screen 28.

Aligned forwardly of objective 32 is light deflector 38, e.g. a plane mirror, prism or other suitable light deflecting means. Deflector 38 establishes a reference plane P from which range finding measurements may be made with fiberscope 10. Reference plane P extends through the point of incidence of optical axis 40 upon deflector 38 and perpendicularly across axis 42 of objective 30. The distance B between axes 40 and 42 being known and fixed, lies in the established reference plane.

Light deflector 38 is carried by gear segment 43 which is in mesh with worm gear 44. Segment 43 is angularly adjustable, i.e. titlable, by rotation of gear 44 with flexible cable 46 and operating knob 48.

It is contemplated that component 12, objectives 30 and 32, light deflector 38, segment 43, gear 44 and cable 46 be supported and contained as a unit preferably in a surrounding flexible sheath S as schematically illustrated with broken lines in FIG. 1. As such, the composite range finding fiberscope 10 may be distally entered into a confined space and operated as follows:

Leg 14 having face 20 is first directed toward a point 50 to be measured and then adjusted laterally to bring an image of the point 50 into centered relationship with crosshairs 34 as viewed on face 24 of screen 28. An image of the same point 50 is then formed and centered upon crosshairs 36 of leg 16 by adjusting the angle of incidence of light deflector 38 relative to plane P. The latter is accomplished remotely through flexible cable 46.

Each increment of angular adjustment of light deflector 38 corresponds to a mechanical position of adjusting knob 48 from which a reading on dial 52 of the distance X between plane P and point 50 may be obtained; $X = (TAN\ \theta)(B)$ where X is the range from point 50 to reference plane P, B equals the aforementioned fixed distance between centers of faces 20 and 22, i.e. between axes 40 and 42, and $\theta$ corresponds to the angular adjustment of light deflector 38.

It should be understood that fiberscope 10 may be rendered remotely distally articulable to facilitate its initial aiming and subsequent alignment of point 50 with crosshairs 34. Examples of means for sheathing and rendering fiberscopes distally articulable can be found in U.S. Pat. Nos. 3,091,235; 3,162,214; and 3,913,568.

Those skilled in the art will readily appreciate that there are various modifications and adaptations of the precise forms of the invention here shown which may be made to meet particular requirements. The foregoing illustrations are not to be interpreted as restrictive of the invention beyond that necessitated by the following claims.

I claim:
1. A range finding instrument comprising:
   a pair of image-conducting bundles of optical fibers each having a distal image-receiving face and a proximal image-emitting face, said proximal faces being juxtapositioned and said distal faces being fixedly spaced a predetermined distance apart in a first plane with axes thereof extending substantially parallel to one another;
   light deflecting means in aligned spaced relationship with a first of said distal faces, said deflecting means intersecting the axis of said first face, the point of said intersection being in a second plane parallel to said first plane, said second plane establishing a reference from which range finding measurements may be made;
   a first objective lens means axially aligned between said deflecting means and said first distal face for focusing an image of a remote object upon said first face;
   second objective lens means axially aligned with the second of said distal faces for focusing an image of said same remote object upon said second face, centering of said image on said second face being accomplished by movement of said instrument;
   means for independently angularly adjusting said light deflecting means relative to said first distal face to center said image of said remote object upon said first distal face; and
   means for determining extent of angulation of said light deflecting means for determination of range of said object from said second plane.

2. A range finding instrument according to claim 1 including reference means on each of said distal image receiving faces relative to which images formed upon said faces by said respective first and second objectives may be centered.

3. A range finding instrument according to claim 1 wherein said means for angularly adjusting said light deflecting means is operatable remotely of said light deflecting means.

4. A range finding instrument according to claim 3 wherein said means for angularly adjusting said light deflecting means is disposed adjacent said proximal image-emitting faces of said bundles of optical fibers.

5. A range finding instrument according to claim 1 wherein said means for angularly adjusting said light deflecting means includes a dial, said dial affording a reading of mechanical increments of angular adjustment of said light deflecting means.

6. A range finding instrument according to claim 5 wherein said dial of said means for adjusting said light deflecting means is disposed remotely of said light deflecting means adjacent said proximal image-emitting faces of said image-conducting bundles and operatively interconnected with said light deflecting means by cable.

7. A range find instrument according to claim 6 wherein said image-conducting bundles and cable are flexible.

8. A range finding instrument according to claim 1 wherein said image-conducting bundles are combined as a unit adjacent said proximal image-emitting faces.

9. A range finding instrument according to claim 1 wherein said image-conducting bundles are flexible intermediately of said image receving and emitting faces thereof.

10. A range find instrument according to claim 7 wherein said image-conducing bundles are contained within a flexible sheath.

* * * * *